United States Patent [19]

Mintchev

[11] Patent Number: 5,922,598
[45] Date of Patent: *Jul. 13, 1999

[54] REDUCING TISSUE IMMUNOGENICITY BY INDUCTION OF APOPTOSIS

[75] Inventor: Milcho S. Mintchev, Gaithersburg, Md.

[73] Assignees: Organ, Inc., Chicago, Ill.; American National Red Cross, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/409,518

[22] Filed: Mar. 24, 1995

[51] Int. Cl.$^6$ ................................................. A61K 45/00
[52] U.S. Cl. ........................... 435/377; 435/1.1; 435/1.2; 424/93.7; 424/278.1
[58] Field of Search ............................. 435/240.2, 377, 435/1.1, 1.2; 530/387.1; 424/93.7, 520, 130.1, 278.1

[56] References Cited

U.S. PATENT DOCUMENTS 5,075,210  12/1991  Wikman et al. ............................. 435/1

FOREIGN PATENT DOCUMENTS

WO93/07900  5/1993  WIPO  ........................ A61K 39/395

OTHER PUBLICATIONS

Merryman Cryobiology, Academic Press, New York, 1966, pp. 75–76.
Goodman et al. (Feb. 1995) Transplantation Proc., vol. 27(1):1347–1348.
Waldmann et al. (1989) Lancet, vol. 2 (8669):935–7.
Spinozzi et al. (1994) Leukemia Research, vol. 18(6):431–439.
Saltzman. (1993) Crit. Rev. Thera. Drug. Carrier Syst. vol. 10(2) : 111–142.
Jocobson, M.D. et al. (1994) EMBO Journal 13(8) 1899–1910.
Richert, L. et al. (1986) Cancer Immunol. Immunother. 22(2) : 119–124.
Vaux, D.L. et al (1994) Cell 76 : 777–779.
M. Rouabhia et al., "Cultured Epithelium Allografts: Langerhans Cell and Thy–1+ Dendritic Epidermal Cell Depletion Effects on Allograft Rejection", *Transplantation*, vol. 56, No. 2, pp. 259–264, (1993).
M. Mincheff et al., "Blood Transfusion and Immunomodulation: A Possible Mechanism", *Vox Sang*, 65:18–24, 1993.
C. B. Thompson, "Apoptosis in the Pathogenesis and Treatment of Disease", *Science*, 267:1456–1462, 1995.
J. Kerr et al, "Definition and Incidence of Apoptosis: An Historical Perspective", Apoptosis: The Molecular Basis of Cell Death, Current Commun. Cell. Molec. Biology, vol. 3, Tomei, L.D. and Cope, F.D., eds., Cold Spring Harbor Laboratory Press, Cold Spring Harbor, New York, 1991.
D. Green et al., "Apoptosis in the Immune System", *Seminars in Immunology*, vol. 4, pp. 355–362, 1992.
H. Steller, "Mechanisms and Genes of Cellular Suicide", *Science*, 267:1445–1449, 1995.

*Primary Examiner*—Christina Y. Chan
*Assistant Examiner*—Patrick J. Nolan
*Attorney, Agent, or Firm*—Oliff & Berridge, PLC

[57] ABSTRACT

A cell is subjected to apoptosis, a genetically programmed autolysis of the cell. Cells of a specific type, classified by function, maturity, source, etc. can be effectively removed from a mixture of cells in a tissue or cell suspension by their different sensitivities to the pressure-time treatment. Donor tissue immunogenicity is eliminated by induction of apoptosis in immunoactive cells, such as antigen presenting cells in the donor tissue. When tissues, for example, blood products containing leukocytes or solid tissues containing dendritic cells, are pressure treated to induce apoptosis in the leukocyte or dendritic cell population, the leukocytes or dendritic cells lose their immunoactivity. Viral particles within the target cells, such as cytomegalovirus particles within the apoptosing leukocytes, are destroyed. Apoptosis can be induced, for example, by subjecting a material containing the target cells to a high pressure.

9 Claims, No Drawings

REDUCING TISSUE IMMUNOGENICITY BY INDUCTION OF APOPTOSIS

BACKGROUND OF THE INVENTION

Fresh tissues contain viable antigen presenting cells which can immunize the recipient against donor tissue antigens and cause graft rejection. This presents problems in matching donors and recipients and is a barrier against interspecies transplantation. Donor antigen presenting cells, for example dendritic cells of the transplanted tissue, present foreign antigens to recipient T cells. A resulting immune response can result in the rejection of the foreign, that is, donor or transplanted, tissue.

In some transplantation procedures, such as those transplanting bone, living cells of the transplanted material are not necessary. The intercellular matrix support is the important component. Bone tissue has been freeze dried, causing necrosis of the cells of the bone matrix. When freeze dried bone tissue is transplanted it is immunoneutral.

There is also particular concern regarding the immunological effects of the antigen-presenting leukocytes that contaminate transfused blood products. In patients receiving subsequent blood transfusions, this immunization can result in febrile transfusion reactions or, in the case of platelet transfusions, the destruction of the platelets.

In response to this problem there is an increasing trend toward the routine filtration of red blood cell and platelet products in order to remove leukocytes. The filters add considerable cost to the blood products, and in addition present their own disposal problem as biohazardous waste. Moreover, even the best filters leave $10^6$ or so leukocytes in the cell suspension.

There is also significant loss of blood product during the filtration procedure. The loss of platelets due to filtration is particularly severe, averaging approximately 25% of the platelet product.

Filtration also does not solve yet another problem associated with leukocytes contaminating blood products, that of transmission of viral diseases in which the viral particles, such as cytomegalovirus, reside within leukocytes. Since filtration leaves approximately $10^6$ leukocytes in suspension, viral particles within these cells are capable of infecting a transfusion recipient.

Heating is another method which has been used for reducing immunogenicity in blood products. A blood product heated to 39° to 40° C. for thirty to sixty minutes demonstrates a reduced immunogenicity, but the mechanisms responsible for this reduction have not been described in the literature.

Exposure to short wavelength light, either UV-B, for platelet products, or gamma radiation, for blood cell products, has been found to reduce immunogenicity. It is difficult to control the exposure throughout the sample, as intensity of the radiation decreases with distance from the source, and the intensity decreases as the radiation is absorbed as it traverses the sample. This exposure also results in the formation of free radicals which can damage extracellular components as well as cells in the sample.

A procedure whereby both the immunoactivity and the threat of infection could be substantially reduced or eliminated would increase the safety of transplanting tissues including the transfusion of blood products.

SUMMARY OF THE INVENTION

Embodiments of the present invention respond to the needs expressed by the problems of the prior art. The invention provides a process wherein a cell of a specific type is subjected to a treatment sufficient to cause cells of that type to apoptose, optionally while sparing cells of other types and any acellular matrix of tissue in the product. When the cell is an immune system cell, such as an antigen presenting cell, immunoneutrality of the accompanying tissue can result. In preferred embodiments, a process is provided which uniformly causes nucleated cells of a type, for example leukocytes, to undergo apoptosis. As part of the process, immunoactivity of the apoptosing cells is eliminated, and DNA within these cells, including viral DNA is disassembled and rendered non-functional.

The process of the invention comprises subjecting a material containing the target cells, such as leukocytes or tissue dendritic, or any other undesired cell capable of undergoing apoptosis, to apoptosis inducing agents such as high pressure, high or low temperature or apoptosis inducing chemical agents. The target cells then begin apoptosis, leading to their destruction.

DETAILED DESCRIPTION OF PREFERRED EMBODIMENTS

The present invention allows transplantation of human or animal tissues, for example, blood, blood products, blood vessels, bone, cornea, cartilage, tendons, ligaments and menisci, across MHC barriers. Even tissues such as organs (e.g., kidney, liver, skin) can be protected by the present invention. The present invention also increases the efficacy and safety of transfusions. For example, a treatment resulting in the selective death and destruction of cells such as leukocytes in a transfusion material such as blood or a portion thereof, or related fluid such as a platelet suspension, would go far to solve problems associated with immunoactivity and the transmission of certain viral diseases. Induction of apoptosis in dendritic cells is also an important embodiment of the invention that can significantly reduce or eliminate rejection of tissue transplants.

One process by which target cells can be destroyed is by the induction of a programmed cell death called apoptosis. Inducing apoptosis in the undesired cells of the transplanted material will allow recipient cells to take their place within the matrix. Thus rejection will not occur. Other cells that may undergo apoptosis with the target cells, e.g., endothelial cells, can also be replaced by recipient cells.

Apoptosis is a genetically controlled process through which the cell self-destructs. Apoptotic cells are immunologically neutral, that is, they induce neither alloimmunization nor immunosuppression. During the self-destruction the cells undergo internal digestion (autolysis) with the concomitant destruction of DNA and other intracellular components.

Apoptosis is involved in antigenic tolerance. A T cell has a different response to an interacting antigen depending on how it is presented. When the antigen is presented by a dendritic cell, the dendritic cell secretes co-stimulatory factors to activate the T cell. However, if the T cell first encounters the interacting antigen in the periphery on a parenchymal cell, that is a non-antigen presenting cell, the T cell apoptoses, thus preventing an autoimmune response. Apoptosis is also involved in tolerance mediated by the thymus gland.

Apoptosis can be induced by physical, for example, heat, UV-B and gamma radiation, and chemical, for example ethanol, treatments. See, e.g., Mincheff, M., et al., Blood Transfusion and Immunomodulation: A Possible Mechanism, *Vox Sang*, 65:18–24, 1993; Thompson, C. D., Apoptosis in the Pathogenesis and Treatment of Disease, *Science*, 267:1456–1462, 1995 which are hereby totally incorporated by reference.

Descriptions of apoptosis and methods for assaying the progression of apoptosis are well known in the art. See, e.g., Apoptosis: *The Molecular Basis of Cell Death*, Current Commun. Cell. Molec. Biology, Vol. 3, Tomei, L. D. and Cope, F. D., eds., Cold Spring Harbor Laboratory Press, Cold Spring Harbor, N.Y., 1991; *Apoptosis in the Immune System*, Green, D. R., ed., Seminars in Immunology, vol. 4, 1992; Stellar, H., Mechanisms and genes of cellular suicide *Science*, 267:1445–1449, 1995, which are hereby totally incorporated herein by reference.

The present invention comprises producing immunoneutrality by inducing apoptosis in cells. In a highly preferred embodiment the invention involves application of high pressure such as high hydrostatic pressure to a material containing the target cells to induce apoptosis, including selective apoptosis, of the target cells.

In a preferred embodiment, one or more liquid filled containers such as bags containing, for example, a cell suspension or a cell containing tissue, is/are placed on a rack inside a pressure vessel such as a bomb. The pressure vessel is filled with fluid, preferably a liquid such as an aqueous solution that excludes undissolved gases from the pressure vessel, then closed. Pressure is increased in the pressure vessel, for example by an automated control system that fills the pressure vessel with the fluid. The pressure is increased to a predetermined pressure and maintained for a predetermined time adequate to induce selective apoptosis of the target cells. After pressurization is ended, the pressure is reduced and the pressure vessel is opened to retrieve the sample container(s). This procedure results in rapid and uniform induction of apoptosis in target cells such as dendritic cells or leukocytes contained in a sample material such as a platelet concentrate product or tissue sample.

Because the effects of pressure are uniform throughout the tissue, pressure has an advantage over UV-B or gamma-irradiation, which are also known to induce apoptosis, but whose intensity attenuates with penetration into the tissue. Pressurization induced apoptosis has an additional advantage because pressurization is less damaging than radiation to non-nucleated tissue components such as extracellular proteins and glycoproteins, comprising a tissue matrix for example.

Pressure induced apoptosis has an advantage over chemical means for inducing apoptosis in that no chemicals remain in the treated tissues.

On the other hand, chemical apoptosis inducing agents may in some cases provide a more desirable level of selectivity. For example, in a whole organ transplant scenario, a dendritic cell apoptosing agent could be bonded to an antibody that selectively recognizes dendritic cells. Exposure of the organ to the antibodies, for example by perfusion, could permit highly selective cell apoptosis without significant damage to organ cells that might undergo apoptosis at high pressures that would cause dendritic cell apoptosis.

Pressure induced apoptosis has an advantage over filtration for removing cells such as immunogenic cells in that no consumables such as filters are used. As a result no additional waste is created. This results in substantial cost savings. Another advantage is that the loss of desired material such as platelets due to the filtration procedure is prevented. Yet another advantage of the present invention over filtration is that the uniform induction of apoptosis can destroy viral particles, such as cytomegalo virus particles, present in the leukocytes. Filtration alone does not inactivate viruses in the leukocytes remaining in the product after filtration.

Apoptosis can also be used in conjunction with filtration. Filtration is used to remove a portion of the target cells. Then activity of the remaining target cells and virus particles, such as cytomegalovirus particles, within the cells is substantially eliminated by inducing apoptosis in the remaining target cells. Alternatively filtration could be conducted after apoptosis occurs to remove remaining undesired materials.

Apoptosis can also be used to inactivate or destroy target cells such as leukocytes and dendritic cells in other products. The process can be applied to any product potentially contaminated by such cells which can survive the pressures or other causative agents used to induce apoptosis of target cells. The process is particularly useful with such products as blood, blood vessels, bone, cornea, cartilage, tendons, ligaments and menisci.

In addition to leukocytes, other cells can be inactivated or destroyed through pressure induced apoptosis. Indeed, any undesired nucleated cell can be eliminated from a tissue, suspension, or culture. For example, tissue dendritic cells can be subjected to apoptosis in accordance with the invention. Platelets and red cells are not susceptible because they have no nuclei and therefore lack the genetic material necessary to carry out apoptosis.

A pressure of 1000 atms for thirty minutes is found to induce apoptosis uniformly in human monocytes. Lower pressures for longer times or higher pressures for shorter times can also be effective. Similarly, different cell types apoptosing in response to pressure display a different susceptibility to the pressure (Table 1). By carefully controlling pressure and exposure time, specific cell types may be destroyed within a tissue or within a mixed suspension of cells while sparing the remaining cells.

TABLE 1

| Cell Type | Pressure | Time | Apoptosis Induction |
|---|---|---|---|
| Human Monocytes | 750 atm | 15 min | (−) |
| Human Monocytes | 750 atm | 3 min | (−) |
| Human Monocytes | 1000 atm | 15 min | (+/−) |
| Human monocytes | 1000 atm | 30 min | (+) |
| Human T cells | 1000 atm | 15 min | (+) |

The pressure exposure conditions sufficient to initiate apoptosis in a specific cell type may be determined by subjecting a tissue or suspension of cells to a chosen apoptosis inducing agent for a chosen time. Also, the exposure to other physical or chemical apoptosis-inducing agents can be used to satisfy or modify the conditions sufficient to cause apoptosis in a selected cell type. Morphologic studies of the various cell types in the tissue or suspension will indicate which cell types are induced to apoptose under the chosen conditions. Thus selection of appropriate agents and conditions can be accomplished by routine experimentation.

While the invention has been described with reference to particular preferred embodiments, the invention is not limited to the specific examples given, and other embodiments and modifications can be made by those skilled in the art without departing from the spirit and scope of the invention.

What is claimed is:

1. A process for inducing apoptosis in a cell of a solid tissue, comprising:
    subjecting the tissue to a pressure of at least 1000 atms for a time sufficient to induce apoptosis in said cell.

2. A process according to claim 1, wherein the solid tissue is selected from the group consisting of bone, cornea, cartilage, tendon, blood vessel, ligament, meniscus and skin.

3. A process according to claim 1, further comprising exposing said tissue to a chemical apoptosis-inducing agent.

4. A process according to claim 1, wherein the tissue comprises an organ.

5. A process for reducing immunogenicity of a donor transplantation tissue and transplanting or transfusing the donor transplantation tissue with reduced immunogenicity, comprising:

isolating a donor transplantation tissue from a donor;

subjecting the isolated donor transplantation tissue to a pressure of at least 1000 atms for a time sufficient to induce apoptosis in an antigen presenting cell in the donor transplantation tissue to reduce immunogenicity of the donor transplantation tissue; and transplanting or transfusing the donor transplantation tissue having reduced immunogenicity to a recipient.

6. A process according to claim 5, wherein the donor transplantation tissue is a blood product.

7. A process according to claim 5, wherein the donor transplantation tissue is a non-blood product.

8. A process according to claim 7, wherein the donor transplantation tissue comprises at least one member selected from the group consisting of bone, cornea, cartilage, tendon, blood vessel, ligament, meniscus and skin.

9. A process according to claim 7, wherein the donor transplantation tissue comprises an organ.

* * * * *